United States Patent [19]

Yamada et al.

[11] Patent Number: 4,969,171
[45] Date of Patent: Nov. 6, 1990

[54] CAT SCANNER

[75] Inventors: Hitoshi Yamada; Ryo Takahashi, both of Tokyo, Japan

[73] Assignee: Yokogawa Medical Systems, Limited, Tokyo, Japan

[21] Appl. No.: 464,636

[22] Filed: Jan. 5, 1990

Related U.S. Application Data

[63] Continuation of Ser. No. 251,222, filed as PCT JP86/00643 on Dec. 19, 1986, published as W087/03796 on Jul. 2, 1987, abandoned.

[30] Foreign Application Priority Data

Dec. 20, 1985 [JP] Japan ................. 60-289069

[51] Int. Cl.$^5$ ............................ H05G 1/60
[52] U.S. Cl. ....................... 378/101; 378/15
[58] Field of Search ................. 378/101–103, 378/15, 105, 107

[56] References Cited

U.S. PATENT DOCUMENTS

| | | | |
|---|---|---|---|
| 4,117,334 | 9/1978 | Strauts | 378/105 |
| 4,171,488 | 10/1979 | Buehnel | 378/105 |
| 4,192,997 | 3/1980 | Baumann | 378/15 |
| 4,221,968 | 9/1980 | Franke | 378/101 |
| 4,221,969 | 9/1980 | Schmidt | 378/101 |
| 4,323,781 | 4/1982 | Baumann et al. | 378/101 |
| 4,368,535 | 1/1983 | Baumann | 378/15 |
| 4,514,795 | 4/1985 | van der Zwarr | 378/105 |
| 4,661,896 | 4/1987 | Isobayashi et al. | 378/101 |
| 4,720,844 | 1/1988 | Bougle | 378/104 |
| 4,783,795 | 11/1988 | Yahara | 378/15 |
| 4,912,735 | 3/1990 | Beer | 378/15 |

Primary Examiner—Carolyn E. Fields
Assistant Examiner—David P. Porta
Attorney, Agent, or Firm—Moonray Kojima

[57] ABSTRACT

A CAT (computerized axial tomography) scanner having a lightweight rotary portion. The scanner has slip rings through which electric power is supplied to an x-ray tube. The slip rings do not need any special insulating mechanism. The scanner includes an inverter (3) for converting a line voltage into an AC voltage between the line voltage and a high voltage applied to the x-ray tube. The frequency of the AC voltage is between the frequency of the line voltage and radio frequencies. This AC voltage is supplied via the slip rings to the rotary portion and then stepped up and rectified by step-up tanks (7, 8) on the rotary portion to obtain the high DC voltage applied to the x-ray tube.

6 Claims, 4 Drawing Sheets

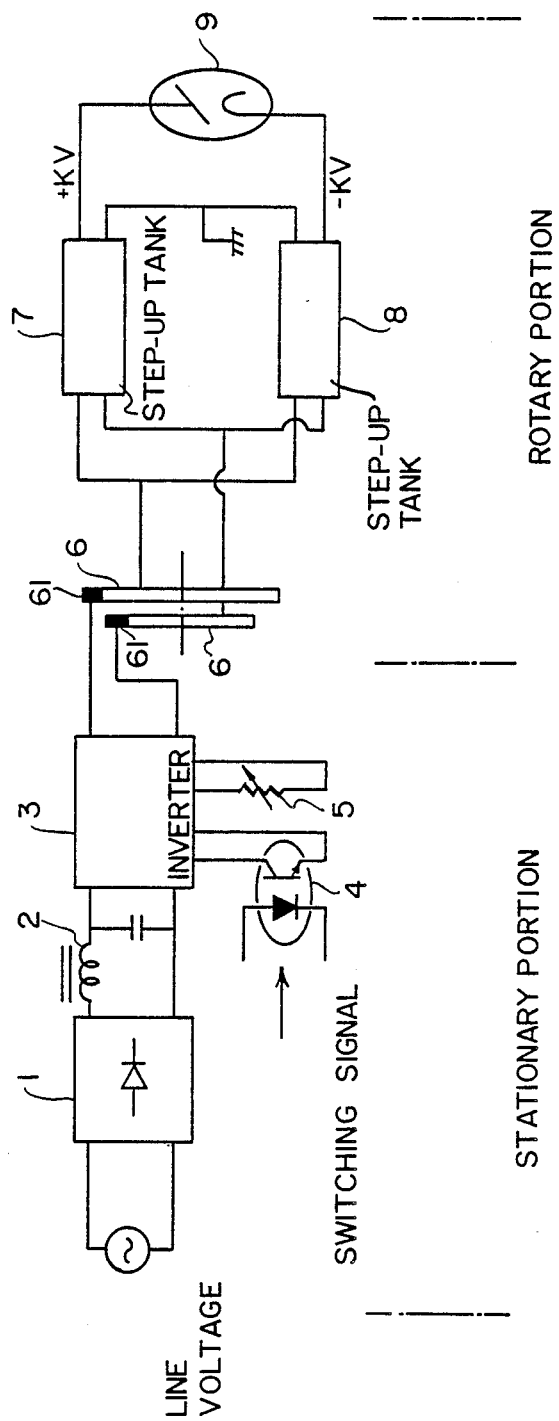

4,969,171

CAT SCANNER

This is a continuation of U.S. patent application Ser. No. 251,222, filed as PCT JP86/00643 on Dec. 19, 1986, published as WO87/03796 on Jul. 2, 1987, now abandoned.

TECHNICAL FIELD

The present invention relates to a CAT (computerized axial tomography) scanner and, more particularly, to a CAT scanner which supplies a high voltage to an x-ray tube mounted on its rotary, portion by an improved method.

BACKGROUND ART

FIG. 4 is a block diagram of main portions of a conventional CAT scanner. This scanner includes an x-ray tube 20 for producing x-rays which are shaped into a sectorial form by a collimator 21 so as to match x-ray detectors 22. An object 23 that is to be examined is inserted in a hole 24. A high-voltage generator portion 25 produces a high voltage that is supplied to the x-ray tube. The rotary portion and the stationary portion of the scanner are indicated by numerals 28 and 29, respectively. The x-ray tube 20, the collimator 21, the x-ray detectors 22, and a data acquisition portion 27 are mounted on the rotary portion 28. The electric power from the high-voltage generator portion 25 is supplied to the x-ray tube 20 on the rotary portion 28 via a slip ring (not shown). In the past, the high voltage that is to be supplied to the tube 20 has been passed through the slip ring. Therefore, the slip ring has required a special insulating material such as an insulating oil or insulating gas.

There exists an improvement over the aforementioned conventional scanner. Specifically, in this improved scanner, a line voltage is directly rectified to produce a DC voltage which is supplied via a slip ring to a high voltage generator mounted on a rotary portion similar to the rotary portion 28 shown in FIG. 4. The high voltage produced by the high voltage generator is supplied to an x-ray tube. The high voltage generator is a DC—DC converter and uses a chopper, for example, to convert its input DC voltage into an RF AC voltage which is then stepped up by a transformer. The AC voltage is doubled and rectified to obtain a high DC voltage. When this method is used, it is only necessary that the slip ring resist a low voltage. Therefore, no special insulating mechanism is needed. However, the mounted DC—DC converter increases the weight of the rotary portion.

DISCLOSURE OF THE INVENTION

It is an object of the invention to provide a CAT (computerized axial tomography) scanner which has slip rings requiring no special insulating mechanism and the rotary portion of which is light in weight.

A CAT scanner according to the invention includes an inverter (3) which converts a line voltage into an intermediate AC voltage between the line voltage and a high voltage applied to an x-ray tube. The frequency of the intermediate voltage is between the frequency of the line voltage and radio frequencies. The intermediate AC voltage is supplied to the rotary portion of the scanner via slip rings (6). The AC voltage is then stepped up and rectified by step-up tanks (7, 8) on the rotary portion to produce a high DC voltage.

BRIEF DESCRIPTION OF THE DRAWINGS

FIG. 1 is a block diagram of a CAT scanner according to the invention;

BEST MODE FOR CARRYING OUT THE INVENTION

Figure 2B:
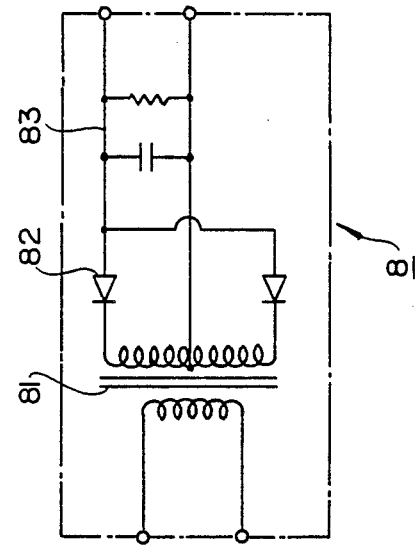
FIGS. 2a and 2b are circuit diagrams of the step-up tanks 7 and 8, respectively, of the scanner shown in FIG. 1.

Referring to FIG. 1, there is shown a CAT scanner embodying the concept of the invention. The scanner has a stationary portion on which a rectifier circuit 1, a smoothing circuit 2, and an inverter 3 are mounted. A line voltage, for example three-phase 200 V of 50 Hz, is rectified by the rectifier circuit 1. The rectified current is passed through the smoothing circuit 2 to obtain a direct current, which is then converted into an alternating current by the inverter 3. The inverter 3 can take any desired form, but a self-excitation inverter that permits the operator to adjust the frequency and the output voltage at will can be used to advantage. It is desired that the waveform of the AC voltage take a sinusoidal form, but rectangular waveforms may also be used. An inverter switching device 4 which is switched on and off by an x-ray switch (not shown) starts and stops the operation of the inverter 3. The output voltage of the inverter 3 is adjusted by a resistor 5. The frequency of the AC output from the inverter 3 does not lie in the radio-frequency range, but is set to a frequency higher than the frequency of the line voltage and within a range of 200 Hz to 2 KHz. The output voltage from the inverter 3 is set to a voltage of several KV which is higher than the line voltage but lower than a high voltage applied to an x-ray tube 9.

The output voltage from the inverter 3 is fed to a pair of slip rings 6 via a pair of brushes 61. The rings 6 act to transmit the output voltage of the inverter 3 from the stationary portion to the rotary portion of the scanner. The voltage applied to the rings 6 is, supplied to step-up tanks 7 and 8 mounted on the rotary portion. The tanks 7 and 8 deliver a high positive voltage and a high negative voltage, respectively. The difference between the output voltage from the step-up tank 7 and the output voltage from the step-up tank 8 is applied to the x-ray tube 9 mounted on the rotary portion. In other embodiments, the sum of the voltages outputted from the tank means 7,8 may be applied to the x-ray tube.

Figure 3:
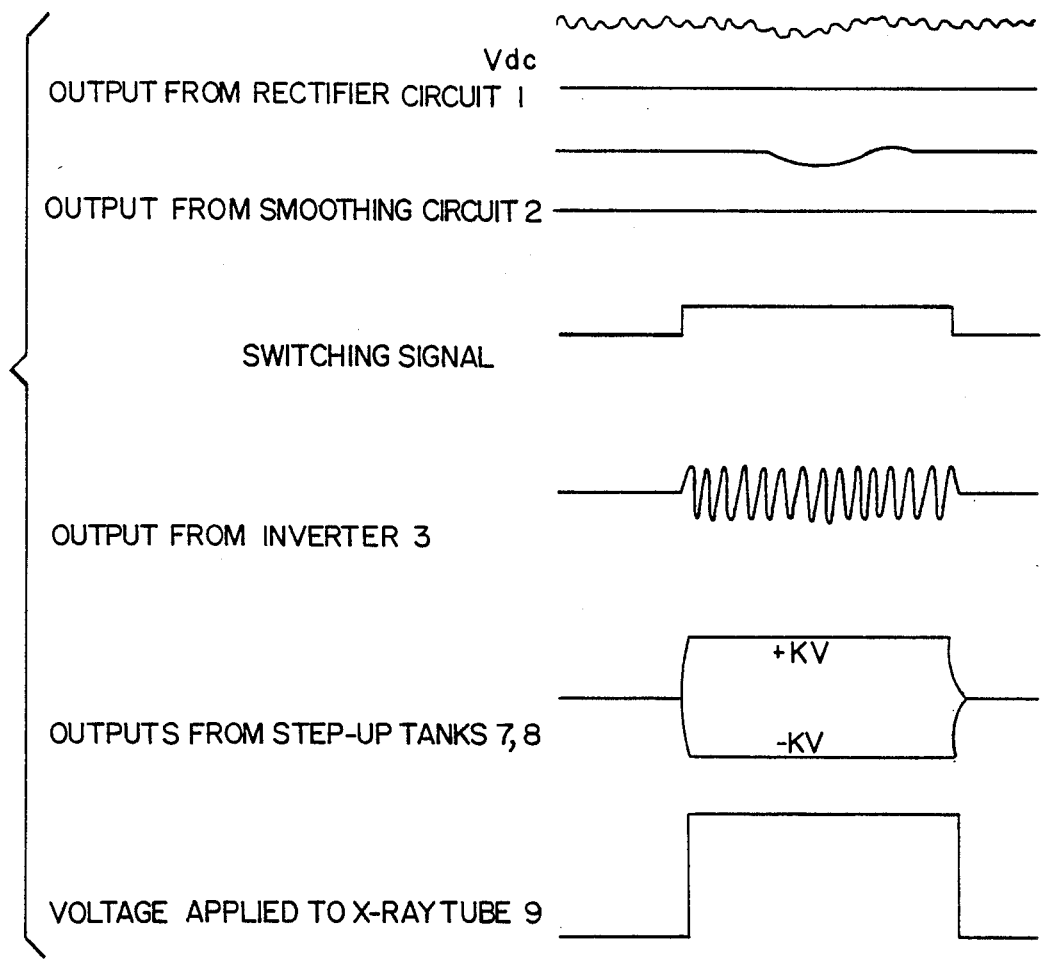
FIG. 3 is a waveform diagram of signals appearing at various locations in the scanner shown in FIG. 1.
Figure 4:
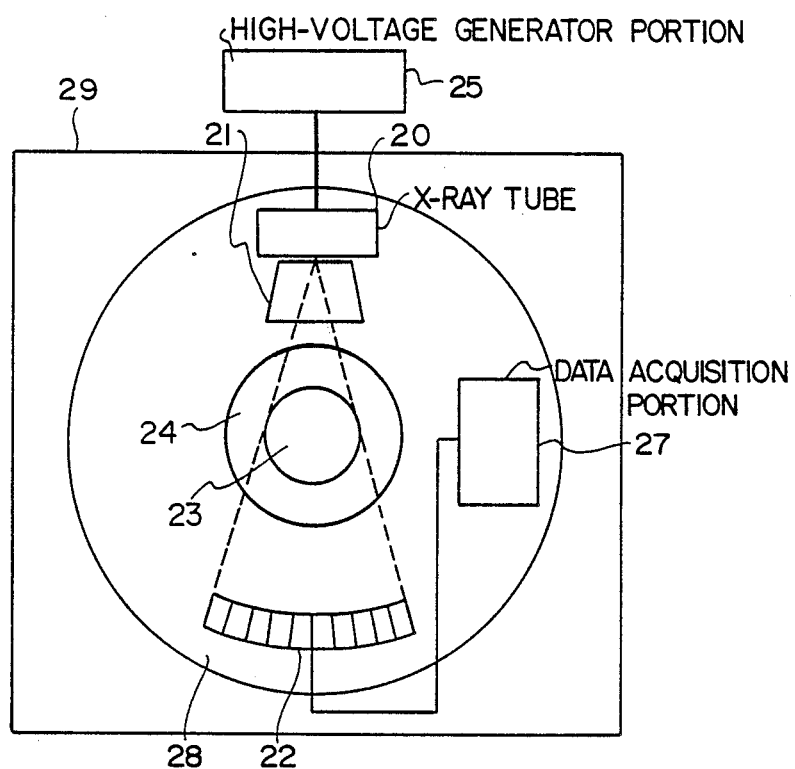
FIG. 4 is a schematic plan view of a conventional CAT scanner.

The operation of the scanner constructed as described above is now described by referring to FIG. 3. The line voltage is rectified by the rectifier circuit 1. The pulsating output voltage from the rectifier circuit 1 is converted by the smoothing circuit 2 into a DC voltage which is supplied to the inverter 3. This inverter 3 is started when the inverter switching device 4 is switched on by a switching signal. The inverter 3 converts its input DC voltage into an AC voltage whose amplitude can be adjusted with the resistor 5. The output voltage from the inverter 3 is automatically regulated so that the line voltage variation appearing on the outputs from the rectifier circuit 1 and the smoothing circuit 2 may not appear on the output from the inverter 3. The output voltage from the inverter 3 is supplied to the slip rings 6 via the brushes 61. The output voltage from the inverter 3 is an intermediate voltage of several, KV which is higher than the line voltage but lower than the high voltage applied to the x-ray tube 9. Any special insulating mechanism including insulating oil or insulating gas for insulating the rings 6 is not needed. The step-up tanks 7 and 8 step up the input voltage supplied via the slip rings 6 to a voltage necessary for the x-ray tube 9, and rectify and smoothen it. Usually, a voltage of 80 to 150 KV is applied to the x-ray tube 9. The tanks 7 and 8 supply voltages that are half that voltage and have opposite polarities to the x-ray tube 9.

Figure 2A:
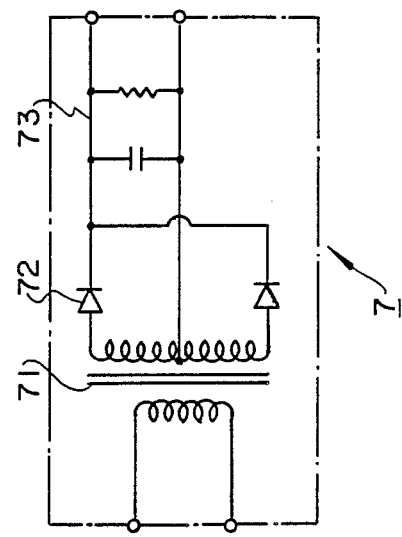

Examples of the circuits of the step-up tanks 7 and 8 are shown in FIGS. 2a and 2b, respectively. Step-up transformers 71 and 81 step up their input voltage of several KV to a voltage of 40 to 75 KV. Therefore, the step-up factor is only 10 to 20, and relatively small-sized lightweight transformers can be used as the transformers 71 and 81. Rectifiers 72 and 82 deliver a positive voltage and a negative voltage, respectively. The tanks 7 and 8 further include smoothing circuits 73 and 83, respectively. The input voltages to the tanks 7 and 8 have a frequency of 200 Hz to 2 KHz which is higher than the frequency of the line voltage. Therefore, the transformers 71 and 81 and the smoothing capacitors of the smoothing circuits 72 and 82 can be made small. This leads to a decrease in the size and weight of the tanks 7 and 8 and so the tanks 7 and 8 are advantageously mounted on the rotary portion. The frequency of the input voltages to the tanks 7 and 8 is not so high as to lie in the radio-frequency range. For this reason, it is not necessary that expensive transformers and rectifiers used in radio-frequency applications be employed as the transformers 71, 81 and the rectifier circuits 72, 82.

It is to be noted that the scanner described above is merely one example of the invention. For example, only one step-up tank may be used. Also, three or more step-up tanks may be employed. In this case, a lower voltage is assigned to each tank.

While the best mode for carrying out the invention has been described, various modifications thereto will occur to those skilled in the art within the scope of the invention which is delineated by the following claims.

We claim:

1. In a CAT scanner comprising a stationary portion, a rotary portion disposed adjacent to said stationary portion and rotatable around an object to be examined, slip rings for electrically connecting together the rotary portion and the stationary portion, an X-ray tube mounted on the rotary portion and supplied with operating voltage via the slip rings for supplying X-rays to the object being examined, X-ray detectors for detecting the X-rays transmitted through the object, and a data acquisition device for collecting data delivered from the detectors; the improvement comprising rectifying and smoothing means mounted on said stationary portion for rectifying and smoothing an AC line voltage for removing variations in said AC line voltage and for producing a DC voltage;

an inverter means mounted on said stationary portion for converting the DC voltage from said rectifying and smoothing means into an intermediate voltage having an intermediate amplitude value between the amplitude value of the AC line voltage and the amplitude value of voltage sufficient to operate said X-ray tube, and an intermediate frequency between the frequency of the AC line voltage and the frequency of radio frequencies, said intermediate voltage being supplied to said slip rings for transmission to the rotary portion;

switching means for selectively operating said inverter means to produce said intermediate voltage having said intermediate amplitude and said intermediate frequency; and transformer and rectifying means mounted on said rotary portion for stepping up and rectifying said intermediate voltage to a DC voltage of sufficient amplitude to operate said X-ray tube.

2. The scanner of claim 1, wherein said switching means comprises a variable resistor for adjusting said amplitude of said intermediate voltage.

3. In a CAT scanner comprising a stationary portion, a rotary portion disposed adjacent to said stationary portion and rotatable around an object to be examined, slip rings for electrically connecting together the rotary portion and the stationary portion, an X-ray tube mounted on the rotary portion and supplied with operating voltage via the slip rings for supplying X-rays to the object being examined, X-ray detectors for detecting the X-rays transmitted through the object, and a data acquisition device for collecting data delivered from the detectors; the improvement comprising rectifying and smoothing means mounted on said stationary portion for rectifying and smoothing an AC line voltage for removing variations in said AC line voltage and for producing a DC voltage;

an inverter means mounted on said stationary portion for converting the DC voltage from said rectifying and smoothing means into an intermediate voltage having an intermediate amplitude value between the amplitude value of the AC line voltage and the amplitude value of voltage sufficient to operate said X-ray tube, and an intermediate frequency between the frequency of the line voltage and the frequency of radio frequencies, said intermediate voltage being supplied to said slip rings for transmission to the rotary portion;

switching means for selectively operating said inverter means to produce said intermediate voltage having said intermediate amplitude and said intermediate frequency; and at least a pair of transformer and rectifying means mounted on said rotary portion for stepping up and rectifying said intermediate voltage to a DC voltage of sufficient amplitude to operate said X-ray tube.

4. The CAT scanner of claim 3, wherein one of said at lest a pair of transformer and rectifying means provides positive output voltage to one terminal of said X-ray tube, and the other of said at least a pair of transformer and rectifying means provides negative output voltage to the other terminal of said X-ray tube, so that the difference between the outputs supplied from said at least a pair of transformer and rectifying means supplies sufficient voltage to operate said X-ray tube.

5. The CAT scanner of claim 3, wherein said at least a pair of transformer and rectifying means are connected to said X-ray tube so that the outputs thereof are applied to supply sufficient amplitude voltage to operate said X-ray tube.

6. The CAT scanner of claim 3, wherein said switching means comprises a variable resistor for adjusting said amplitude of said intermediate voltage.

* * * * *